United States Patent
Mizutani

(10) Patent No.: US 6,296,628 B1
(45) Date of Patent: Oct. 2, 2001

(54) SANITARY NAPKIN

(75) Inventor: Satoshi Mizutani, Kagawa-ken (JP)

(73) Assignee: Uni-Charm Corporation (JP)

( * ) Notice: Subject to any disclaimer, the term of this patent is extended or adjusted under 35 U.S.C. 154(b) by 0 days.

(21) Appl. No.: 09/312,144

(22) Filed: May 14, 1999

(30) Foreign Application Priority Data

May 14, 1998 (JP) ................................. 10-131701

(51) Int. Cl.⁷ ...................................................... A61F 13/15
(52) U.S. Cl. ................ 604/387; 604/385.03; 604/385.16
(58) Field of Search ................................... 604/354, 387, 604/385.03, 385.14, 385.16

(56) References Cited

U.S. PATENT DOCUMENTS

| | | | |
|---|---|---|---|
| 4,425,130 | * | 1/1984 | DesMarais ............................ 604/389 |
| 5,599,337 | * | 2/1997 | Mccoy ................................ 604/385.1 |
| 5,695,324 | * | 12/1997 | Weirich ................................ 604/378 |
| 5,702,375 | * | 12/1997 | Angelillo et al. ..................... 604/358 |
| 5,743,896 | * | 4/1998 | Parker ................................ 604/385.1 |
| 5,853,401 | * | 12/1998 | Mayer et al. ........................ 604/378 |
| 5,873,869 | * | 2/1999 | Hammons et al. ................ 604/385.1 |

FOREIGN PATENT DOCUMENTS

| | | |
|---|---|---|
| 0606082 | 7/1994 | (EP) . |
| 0904755 | 3/1999 | (EP) . |

* cited by examiner

Primary Examiner—Aaron J. Lewis
Assistant Examiner—Michael Bogart
(74) Attorney, Agent, or Firm—Baker & Daniels

(57) ABSTRACT

A sanitary napkin comprising a first member including a liquid-pervious topsheet, a liquid-impervious backsheet and a first liquid-absorbent core disposed therebetween and a second member including a substantially liquid-pervious and elastically stretchable/contractile sheets and a second liquid-absorbent core covered with the elastically stretchable/contractile sheets, wherein the first and second members respectively have a longitudinal direction extending between their opposite side end portions and a transverse direction extending between their opposite side edge portions, the second member being placed upon and joined under tension in the longitudinal direction to an upper surface of the first member at their respective front and rear end portions.

8 Claims, 3 Drawing Sheets

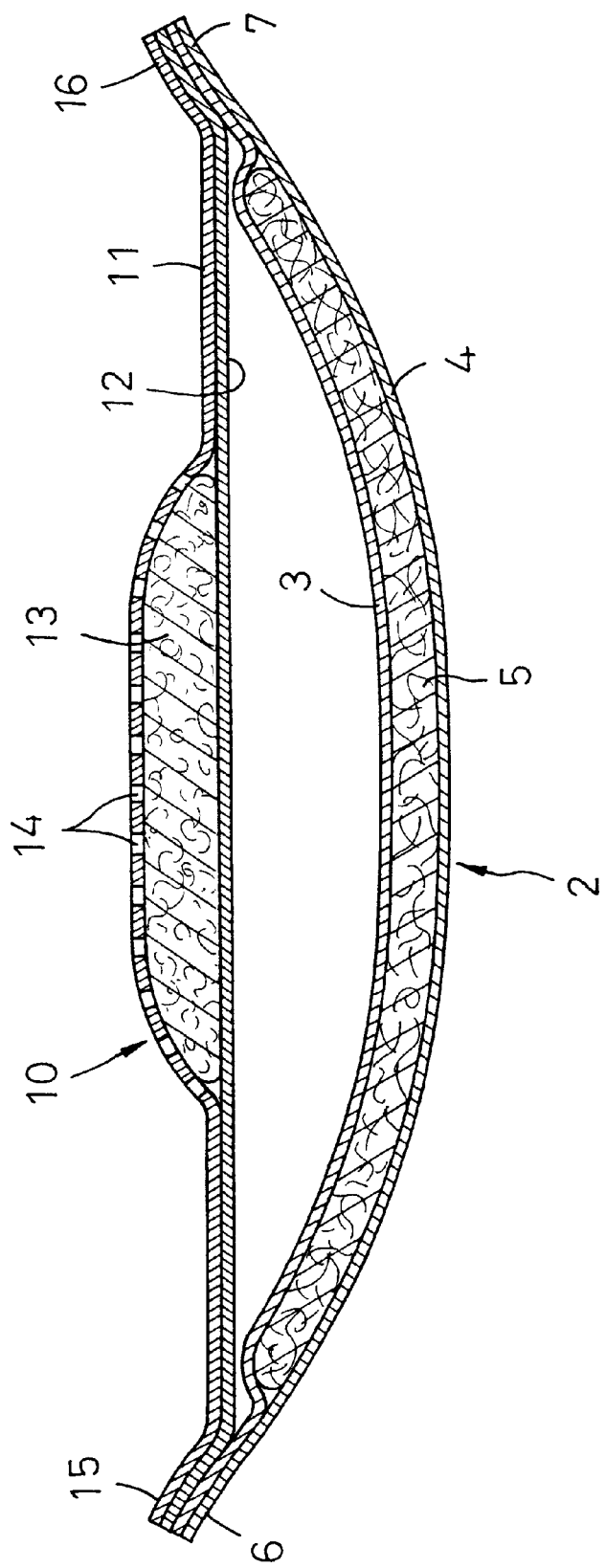

SANITARY NAPKIN

BACKGROUND OF THE INVENTION

The present invention relates to sanitary napkins or menstruation pads for absorption and containment of body exudates.

Sanitary napkins are usually worn by fastening a adhesive zone provided on a bottom surface of the napkin to a crotch region of an undergarment worn by a wearer.

The known napkin tends to slip down as the undergarment slips down and consequently the napkin is spaced from the wearer's vaginal orifice and the vicinal area. This may often cause undesirable leakage of body exudates.

SUMMARY OF THE INVENTION

In view of this problem, it is an object of the present invention to provide a novel sanitary napkin adapted to eliminate leakage of body exudates due to the foregoing cause.

According to the present invention, there is provided a sanitary napkin comprising a first member including a liquid-pervious topsheet, a liquid-impervious backsheet and a first liquid-absorbent core disposed between the topsheet and the backsheet and a second member including a substantially liquid-pervious and elastically stretchable/contractile sheets and a second liquid-absorbent core occupying a central zone of the second member and covered with the elastically stretchable/contractile sheets, wherein: the first and second members respectively have a longitudinal direction extending between front and rear end portions thereof and a transverse direction extending between opposite side edge portions, the second member being placed upon and joined under tension in the longitudinal direction to an upper surface of the first member at the respective front and rear end portions.

According to an embodiment of the present invention, the opposite side edge portions of the first member extend outward beyond the corresponding opposite side edge portions of the second member. In this embodiment, the second member has an elongation percentage of 5~50% and a contractile force of 11.8~196.9 g/cm both in the longitudinal direction. Preferably, the presence of the second core causes the central zone of the second member to protrude upward.

BRIEF DESCRIPTION OF THE DRAWINGS

FIG. 3 is a sectional view taken along a line B—B.

DETAILED DESCRIPTION OF THE PREFERRED EMBODIMENTS

Details of a sanitary napkin according to the present invention will be more fully understood from the description given hereunder with reference to the accompanying drawings.

Figure 1:
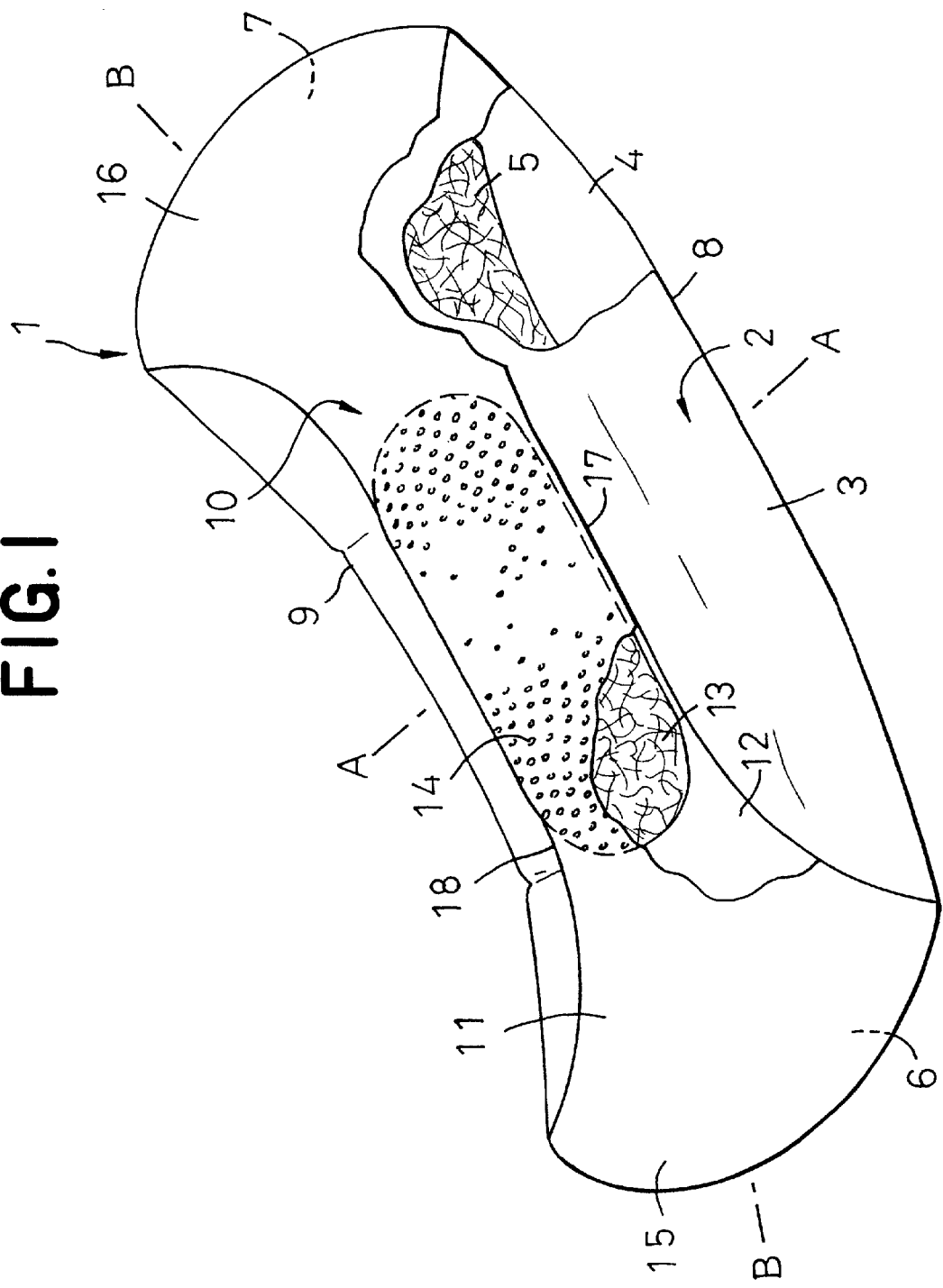
FIG. 1 is a perspective view of a sanitary napkin constructed according to one embodiment of the present invention having partly cut away portions.
Figure 2:
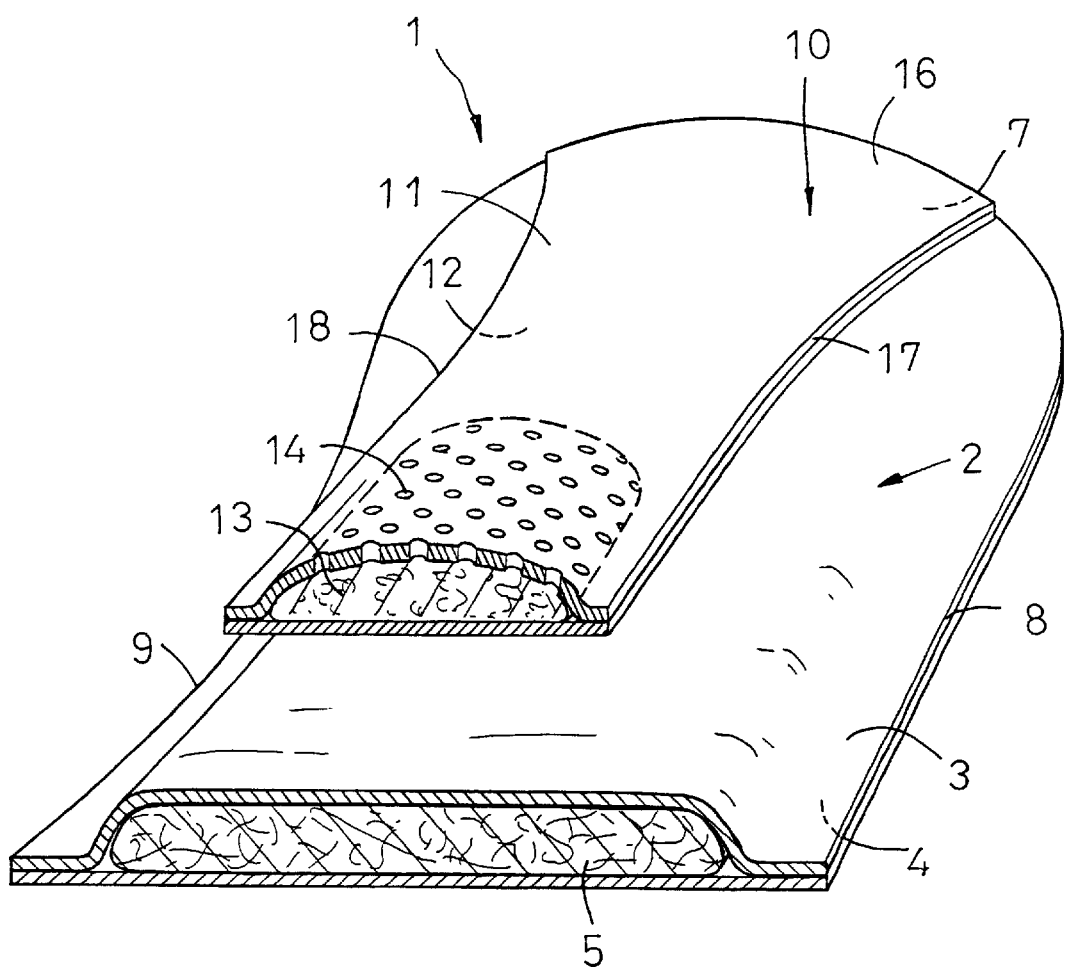
FIG. 2 is a perspective view of the sanitary napkin in a section as viewed along a line A—A in FIG. 1.

FIG. 1 is a perspective view of a sanitary napkin 1 having partly cut away portions and FIG. 2 is a perspective view of this sanitary napkin 1 in a section as viewed along a line A—A in FIG. 1. Basically, the sanitary napkin 1 comprises a first member 2 and a second member 10 placed upon the first member 2. Placing the second member 10 under longitudinal tension, its longitudinally opposite end portions are joined to longitudinally opposite end portions of the first member 2 so that the second member 10 causes the first member 2 to be longitudinally curved downward as the second member 10 elastically contracts.

The first member 2 comprises a liquid-pervious topsheet 3, a liquid-impervious backsheet 4 and a first liquid-absorbent core 5 disposed between these two sheets 2, 3. The first core 5 may be bonded to an inner surface of at least one of the topsheet 2 and the backsheet 3, if desired. Portions of the topsheet 2 and the backsheet 3 extending outward beyond a peripheral edge of said first core 5 are placed upon and bonded to each other by means of a suitable adhesive agent or heat-sealing technique.

The second member 10 comprises liquid-pervious and elastic sheets 11, 12 and a second liquid-absorbent core 13 disposed between these two sheets 11, 12. The second core 13 may be bonded to an inner surface of at least one of the two sheets 11, 12. Portions of these sheets 11, 12 extending outward beyond a peripheral edge of the second core 13 are placed upon and bonded to each other by means of a suitable adhesive agent or heat-sealing technique. The second core 13 occupies a central zone of the second member 10 between the elastic sheets 11, 12 and consequently the central zone of the second member 10 protrudes. The elastic sheet 11 covering a top surface of the second core 13 is formed in the central zone corresponding to the second core 13 with a plurality of liquid-pervious apertures 14.

The first member 2 and the second member 10 have longitudinally opposite end portions 6, 7 and 15, 16 and transversely opposite side edge portions 8, 17 and 9, 18, respectively. The end portions 6, 15 and 7, 16 are placed in front and rear portions, respectively, of an undergarment worn by a wearer and extend transversely of the napkin. The transversely opposite side edge portions 8, 17 and 9, 18 extend longitudinally along transversely opposite side edge portions of a crotch region of the undergarment. In proximity of the central zone, the second member 10 has a transversely dimension smaller than the corresponding dimension of the first member 2 and the second core 13 also has a transversely dimension smaller than the corresponding dimension of the first core 5.

Placing the second member 10 under longitudinal tension, its longitudinally opposite end portions 15, 16 are joined to the longitudinally opposite end portions 6, 7 of the first member 2 on an upper surface thereof. Such operation of joining may be achieved by means of a known heat-sealing technique or the suitable adhesive agent. An elongation percentage between the front and rear end portions 15, 16 of the second member 10 is adjusted to lie in a range of 5~50% and a contractile force generated from this elongated state is adjusted to lie in a range of 11.8~196.9 g/cm, preferably, in a range of 11.8~118.1 g/cm.

FIG. 3 is a sectional view of the sanitary napkin taken along a line B—B in FIG. 1, as the second member 10 is released to contract. With the napkin 1 of such construction, a contractile force of the second member 10 causes the first member 2 to be longitudinally curved downward against a rigidity of the first member 2 as the napkin 1 is unpacked before its actual use. Thereupon, the second member 10 extend practically in a horizontal direction between the front and rear end portions 15, 16 of the elastic sheets 11, 12 and tends to be spaced upward from the topsheet 3 of the first member 2 except at the front and rear end portions 15, 16 of the elastic sheets 11, 12.

With the napkin 1 is pressed against a wearer's body, the first and second members 2, 10 which are normally kept entirely in contact with each other are placed against the wearer's crotch zone. However, the first member 2 may be spaced from the wearer's crotch zone if the undergarment on which the napkin 1 is fastened unintentionally slips down. Even in such situation, the central zone of the second member 10 remains in contact with the wearer's crotch zone and the second core 13 of the second member 10 effectively absorbs body exudates. In consequence, there is no apprehension that leakage of body exudates might occur. An amount of body exudates which has not been absorbed by the second core 13 is reliably absorbed by the first core 5 of the first member 2 underlying the second member 10.

While various types of material are available for the elastic sheets 11, 12 forming the second member 10, the material to be used is preferably selected from a group including an apertured sheet obtained by subjecting a elastic film mixed with synthetic rubber to a laser-, heat emboss- or slit widening-treatment, a spun bond nonwoven fabric or a melt blown nonwoven fabric both of synthetic rubber, a laminate of elastic material and nonwoven fabric, etc. The second core 13 is transversely dimensioned to be preferably in a range of 10~60 mm, more preferably in a range of 20~40 mm. The second core 13 is longitudinally dimensioned to be preferably 50 mm or more. The second core 13 preferably has a thickness of 10~15 mm. Both the first and second cores 5, 13 preferably contain superabsorptive polymer particles and a content density and/or an absorption rate thereof is preferably higher in the second core 13 than in the first core 5. Preferably, a zone of the second member 10 occupied by the second core 13 has a cross-section which progressively protrudes from the side edges toward the middle and is softer than a zone of the first member 2 occupied by the first core 5.

The longitudinally opposite end portions 15, 16 of the second member 10 are joined to an upper surface of the topsheet 3 over portions thereof which extend outward beyond a peripheral edge of the first core 5. In this case, the end portions 15, 16 of the second member 10 to be joined to the upper surface of the topsheet 3 may be accurately placed upon the corresponding end portions of the first core 5 to facilitate the latter 5 to be longitudinally curved downward under a contractile force of the second member 10. The first core 5 may be intermittently bonded to the topsheet 3 in order to avoid an apprehension that the topsheet 3 and the first core 5 might be spaced from each other as the first member 2 is longitudinally curved downward.

With the novel sanitary napkin, leakage of body exudates is reliably avoided even when the undergarment worn by a wearer slips down during use of the napkin and the first member is spaced from the wearer's crotch zone. This is ensured by the unique arrangement wherein the second member is always elastically spaced upward from the first member so as to be placed against the wearer's crotch zone. In addition, the first and second members are adapted to be relatively movable in the longitudinal direction as well as in the transverse direction, particularly in the transverse direction of the napkin. Accordingly, the second member is reliably held to be placed against the wearer's crotch zone even when the first member transversely moves together with the undergarment, and thereby leakage of body exudates due to such transverse movement of the first member is prevented from occurring.

What is claimed is:

1. A sanitary napkin comprising:

a first member including a liquid-pervious topsheet, a liquid-impervious backsheet and a first liquid-absorbent core disposed between said topsheet and said backsheet; and a second member including substantially liquid-pervious and elastically stretchable/contractile sheets and a second liquid-absorbent core occupying a central zone of said second member between said elastically stretchable/contractile sheets, said first and second members respectfully having a longitudinal direction extending between front and rear end portions thereof and a transverse direction extending between opposite side edge portions, said second member being placed upon and joined under tension in said longitudinal direction to an upper surface of said first member at said respective front and rear end portions, so that said second liquid-absorbent core is caused to become spaced apart from said first liquid-absorbent core due to said tension.

2. A sanitary napkin according to claim 1, wherein said opposite side edge portions of said first member extend outward beyond adjacent opposite side edge portions of said second member.

3. A sanitary napkin according to claim 1, wherein said second member has an elongation percentage of about 5 to about 50% in said longitudinal direction and a contractile force of about 11.8 to about 196.9 g/cm in said longitudinal direction.

4. A sanitary napkin according to claim 1, wherein said second liquid-absorbent core causes said central zone of said second member to protrude upward.

5. A sanitary napkin comprising:

a first member including a liquid-pervious topsheet, a liquid-impervious backsheet and a first liquid-absorbent core disposed between said topsheet and said backsheet; and a second member including substantially liquid-pervious and elastically stretchable/contractile sheets and a second liquid-absorbent core occupying a central zone of said second member between said elastically stretchable/contractile sheets, said first and second members respectfully having a longitudinal direction extending between front and rear end portions thereof and a transverse direction extending between opposite side edge portions, said second member being placed upon and joined under tension in said longitudinal direction to an upper surface of said first member exclusively at said respective front and rear end portions.

6. A sanitary napkin according to claim 5, wherein said opposite side edge portions of said first member extend outward beyond adjacent opposite side edge portions of said second member.

7. A sanitary napkin according to claim 5, wherein said second member has an elongation percentage of about 5 to about 50% in said longitudinal direction and a contractile force of about 11.8 to about 196.9 g/cm in said longitudinal direction.

8. A sanitary napkin according to claim 5, wherein said second liquid-absorbent core causes said central zone of said second member to protrude upward.

* * * * *